United States Patent
Xu et al.

(10) Patent No.: US 10,549,242 B2
(45) Date of Patent: Feb. 4, 2020

(54) PLASMA EXTRACTOR

(71) Applicant: Becton, Dickinson and Company, Franklin Lakes, NJ (US)

(72) Inventors: Qihua Xu, Cary, NC (US); Alexander G. Lastovich, Raleigh, NC (US)

(73) Assignee: Becton Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 15/565,326

(22) PCT Filed: Jun. 7, 2016

(86) PCT No.: PCT/US2016/036209
§ 371 (c)(1),
(2) Date: Oct. 9, 2017

(87) PCT Pub. No.: WO2016/200806
PCT Pub. Date: Dec. 15, 2016

(65) Prior Publication Data
US 2018/0056243 A1    Mar. 1, 2018

Related U.S. Application Data

(60) Provisional application No. 62/172,424, filed on Jun. 8, 2015.

(51) Int. Cl.
*B01D 63/06* (2006.01)
*B01D 63/16* (2006.01)
*B01D 69/02* (2006.01)
*B01D 71/50* (2006.01)

(52) U.S. Cl.
CPC .......... *B01D 63/16* (2013.01); *B01D 63/062* (2013.01); *B01D 69/02* (2013.01); *B01D 71/50* (2013.01);
(Continued)

(58) Field of Classification Search
CPC . A61M 1/262; A61M 1/3496; B01D 2313/04; B01D 2315/02; B01D 2315/04;
(Continued)

(56) References Cited

U.S. PATENT DOCUMENTS

| | | | |
|---|---|---|---|
| 4,066,554 A | * | 1/1978 | Guyer .................. B01D 33/073 210/342 |
| 4,740,313 A | | 4/1988 | Schoendorfer et al. |

(Continued)

FOREIGN PATENT DOCUMENTS

| | | |
|---|---|---|
| EP | 0403031 A2 | 12/1990 |
| EP | 0464707 A2 | 1/1992 |

(Continued)

OTHER PUBLICATIONS

Japanese Official Notice of Rejection issued in corresponding JP application No. 2017-563527 dated Oct. 23, 2018.
(Continued)

*Primary Examiner* — Pranav N Patel
(74) *Attorney, Agent, or Firm* — Botos Churchill IP Law LLP (57) ABSTRACT

A filtration cell (10) for a biological sample having an outer housing (12) defining a first chamber and an inner housing (14) defining a second chamber is disclosed. The inner housing is disposed within the first chamber and rotatable with respect to the outer housing and at least a portion of the inner housing includes a filtration membrane (52). Upon rotation of the inner housing, a first portion of the biological sample passes from the first chamber into the second chamber and a second portion of the biological sample is restrained in the first chamber. Alternatively, the filtration cell may also include a rotation element disposed in the inner housing. Upon rotation of the rotation element with respect to the inner housing, a first portion of the biological sample
(Continued)

to passes from the second chamber into the first chamber and a second portion of the biological sample is restrained in the second chamber.

22 Claims, 6 Drawing Sheets

(52) U.S. Cl.
CPC ...... *B01D 2313/04* (2013.01); *B01D 2315/02* (2013.01); *B01D 2325/04* (2013.01); *B01D 2325/06* (2013.01)

(58) Field of Classification Search
CPC ............ B01D 2325/04; B01D 2325/06; B01D 61/147; B01D 61/18; B01D 63/062; B01D 63/16; B01D 69/02; B01D 71/50
See application file for complete search history.

(56) References Cited

U.S. PATENT DOCUMENTS

| | | | |
|---|---|---|---|
| 4,871,462 A | 10/1989 | Fischel et al. | |
| 5,034,135 A | 7/1991 | Fischel | |
| 2004/0251214 A1* | 12/2004 | Adams | B01D 33/073 210/695 |
| 2013/0334139 A1* | 12/2013 | Blickhan | A61M 1/0272 210/650 |
| 2015/0060363 A1 | 3/2015 | Kusters et al. | |

FOREIGN PATENT DOCUMENTS

| | | |
|---|---|---|
| EP | 2842619 A1 | 3/2015 |
| JP | HEI 03-247345 | 11/1991 |
| WO | 19910001796 A1 | 2/1991 |
| WO | 20000050157 A1 | 8/2000 |

OTHER PUBLICATIONS

ISR and Written Opinion for Application No. PCT/US2016/036209 dated Aug. 25, 2016.

Jaffrin MY: Innovative Processes for Membrane Plasma Separation 11, Journal of Membrane Science, Elsevier BV, NL, vol. 44, No. 1, Jun. 1, 1989 (Jun. 1, 1989), pp. 115-129, XP000068839, ISSN: 0376-7388, DOI: 10.1016/S0376-7388(00)82344-3, pp. 123-124.

* cited by examiner

PLASMA EXTRACTOR

CROSS-REFERENCE TO RELATED APPLICATION

This application is the United States national phase of International Application No. PCT/US2016/036209, filed Jun. 7, 2016, entitled "Plasma Extractor", and claims priority to U.S. Provisional Application Ser. No. 62/172,424, filed Jun. 8, 2015, entitled "Plasma Extractor From Whole Blood", the entire disclosure of which is hereby incorporated by reference.

BACKGROUND OF THE INVENTION

1. Field of the Invention

The present invention relates to a filtration cell and a method for filtering a biological sample and, specifically, to a filtration cell and a method for filtering a plasma portion from a whole blood sample.

2. Description of Related Art

Conventionally, centrifuging of whole blood samples has been used for plasma extraction from the whole blood sample. However, recent developments in diagnostics, particularly in near patient care or point-of-care (POC) testing has presented many challenges for this conventional technique. Near patient blood testing often requires rapidly obtained test results with small volume collection samples, for example, a blood sample collected using a capillary draw. Therefore, other techniques including filtering, hydrodynamic branch flow extraction, dielectrophoresis separation, acoustic focusing, and magnetic separation have been developed. However, all of these methods have various limitations. For example, many of these methods have one or more drawbacks including the need for high fold dilution, reliance on external hardware, lower plasma yield, long separation times, high cellular contamination, and significant sample hemolysis.

Specifically, track etched membranes have been used to separate a plasma portion from whole blood. The advantage of track etched membranes is the uniform pore size and relatively small surface area as compared to other filtration membranes. The potential low non-specific binding characteristics of track etched membranes is very attractive for detecting low concentration analytes such as troponin in a cardiac patient. While direct filtration using track etched membranes is limited due to clotting, a tangential flow process has shown much better performance. A multi-pass reciprocating process using a track etched membrane to extract plasma from whole blood outperforms other cross flow hydrodynamic based technologies in plasma yield, cellular contamination, and separation time. However, the system requires a complicated power mechanism and control system including optical sensors.

Therefore, a need exists for a simplified system that can easily be used for near patient care or point-of-care (POC) testing

SUMMARY OF THE INVENTION

The present invention is directed to a filtration cell for a biological sample having an outer housing having a first end, a second end, and a sidewall extending therebetween and defining a first chamber and an inner housing having a first end, a second end, and a sidewall extending therebetween and defining a second chamber. The inner housing is disposed within the first chamber and rotatable with respect to the outer housing and at least a portion of the inner housing includes a filtration membrane. Upon rotation of the inner housing with respect to the outer housing, the filtration membrane is adapted to allow a first portion of the biological sample to pass from the first chamber into the second chamber and to restrain a second portion of the biological sample in the first chamber. The filtration cell may further include a closure sealing the first end of the outer housing and the first end of the inner housing.

Rotation of the inner housing with respect to the outer housing causes a tangential flow of the biological sample contained in the first chamber over the filtration membrane of the inner housing. The rotation axis of the inner housing may be coaxial with a central axis of the outer housing or the rotation axis of the inner housing may be offset from a central axis of the outer housing. The rotation may be provided by a biasing member acting on the inner housing. The biasing member may be a spring. In certain embodiments, the inner housing may be movable in a direction parallel to a central axis of the outer housing.

In certain embodiments, a pressure differential may be created across the filtration membrane by introducing a positive pressure into the first chamber or by creating a vacuum in the second chamber.

In certain embodiments, an inner surface of the outer housing sidewall may include grooves and/or include a port for receiving the biological sample.

The filtration cell may further include an air-permeable liquid seal between an interior surface of the sidewall of the outer housing and an exterior surface of the sidewall of the inner housing.

In some embodiments, the distance from the first end of the outer housing to the second end of the outer housing may be larger than the diameter of the outer housing and the distance from the first end of the inner housing to the second end of the inner housing may be larger than a diameter of the inner housing. In other embodiments, the distance from the first end of the outer housing to the second end of the outer housing may be smaller than the diameter of the outer housing and the distance from the first end of the inner housing to the second end of the inner housing may be smaller than the diameter of the inner housing.

In certain embodiments, the filtration membrane may be a track-etched membrane. In other embodiments, the filtration membrane may be a fibrous membrane.

The present invention is also directed to a method of filtering a biological sample. A biological sample is placed in the first chamber of a filtration cell as described above. The inner housing of the filtration cell is rotated with respect to the outer housing, and a filtrate is collected in the second chamber.

In certain embodiments, a pressure differential may be created across the filtration membrane by introducing a positive pressure into the first chamber or by creating a vacuum in the second chamber. In other embodiments, the inner housing may be moved in a direction parallel to a central axis of the outer housing while it is being rotated.

A biasing member may rotationally bias the inner housing with respect to the outer housing. The biasing member may be a compression spring or a torsional spring. An engagement element may hold the biasing member in a biased position and release of the engagement element and the biasing member may provide the rotational force to the inner housing.

The present invention is also directed to a filtration cell for a biological sample including an outer housing having a first end, a second end, and a sidewall extending therebetween and defining a first chamber, an inner housing having a first end, a second end, and a sidewall extending therebetween and defining a second chamber, and a rotation element rotatable with respect to the outer housing and the inner housing. The inner housing is disposed within the first chamber and the rotation element is disposed within the second chamber. At least a portion of the inner housing is a filtration membrane. Upon rotation of the inner housing with respect to the outer housing, the filtration membrane is adapted to allow a first portion of a biological sample to pass from the second chamber into the first chamber and to restrain a second portion of the biological sample in the second chamber. The filtration cell may further include a closure sealing the first end of the outer housing and the first end of the inner housing.

Rotation of the rotation element with respect to the inner housing causes a tangential flow of the biological sample contained in the second chamber over the filtration membrane of the inner housing. The rotation axis of the rotation element may be coaxial with a central axis of the inner housing or the rotation axis of the rotation element may be offset from a central axis of the inner housing. The rotation may be provided by a biasing member acting on the rotation element. The biasing member may be a compression spring or a torsional spring. In certain embodiments, the rotation element may be movable in a direction parallel to a central axis of the outer housing.

In certain embodiments, a pressure differential may be created across the filtration membrane by introducing a positive pressure into the second chamber or by creating a vacuum in the first chamber.

In certain embodiments, the outer housing sidewall may include a port for extracting the filtered portion of the biological sample. In other embodiments, the rotation element may include grooves.

The filtration cell may further include an air-permeable liquid seal between an interior surface of the sidewall of the outer housing and an exterior surface of the sidewall of the inner housing.

In some embodiments, the distance from the first end of the outer housing to the second end of the outer housing may be larger than the diameter of the outer housing and the distance from the first end of the inner housing to the second end of the inner housing may be larger than a diameter of the inner housing. In other embodiments, the distance from the first end of the outer housing to the second end of the outer housing may be smaller than the diameter of the outer housing and the distance from the first end of the inner housing to the second end of the inner housing may be smaller than the diameter of the inner housing.

In certain embodiments, the filtration membrane may be a track-etched membrane. In other embodiments, the filtration membrane may be a fibrous membrane.

The present invention is also directed to a method of filtering a biological sample. A biological sample is placed in the second chamber of a filtration cell as described above. The rotation element of the filtration cell is rotated with respect to the inner housing, and a filtrate is collected in the first chamber.

In certain embodiments, a pressure differential may be created across the filtration membrane by introducing a positive pressure into the second chamber or by creating a vacuum in the first chamber. In other embodiments, the rotation element may be moved in a direction parallel to a central axis of the inner housing while it is being rotated.

A biasing member may provide the rotational force to the rotation element. The biasing member may be a compression spring or a torsional spring. An engagement element may hold the biasing member in a biased position and release of the engagement element and the biasing member may provide the rotational force to the rotation element.

DESCRIPTION OF THE INVENTION

The present invention is directed to a filtration cell for a biological sample and a method of filtering a biological sample for the purpose of isolating one component or fraction of a biological sample from another component or fraction of the sample. In one configuration, the biological sample may include whole blood from which a plasma portion is to be separated.

As shown in FIGS. 1-5B, the filtration cell 10 includes an outer housing 12, an inner housing 14, and a closure 16.

Figure 1:
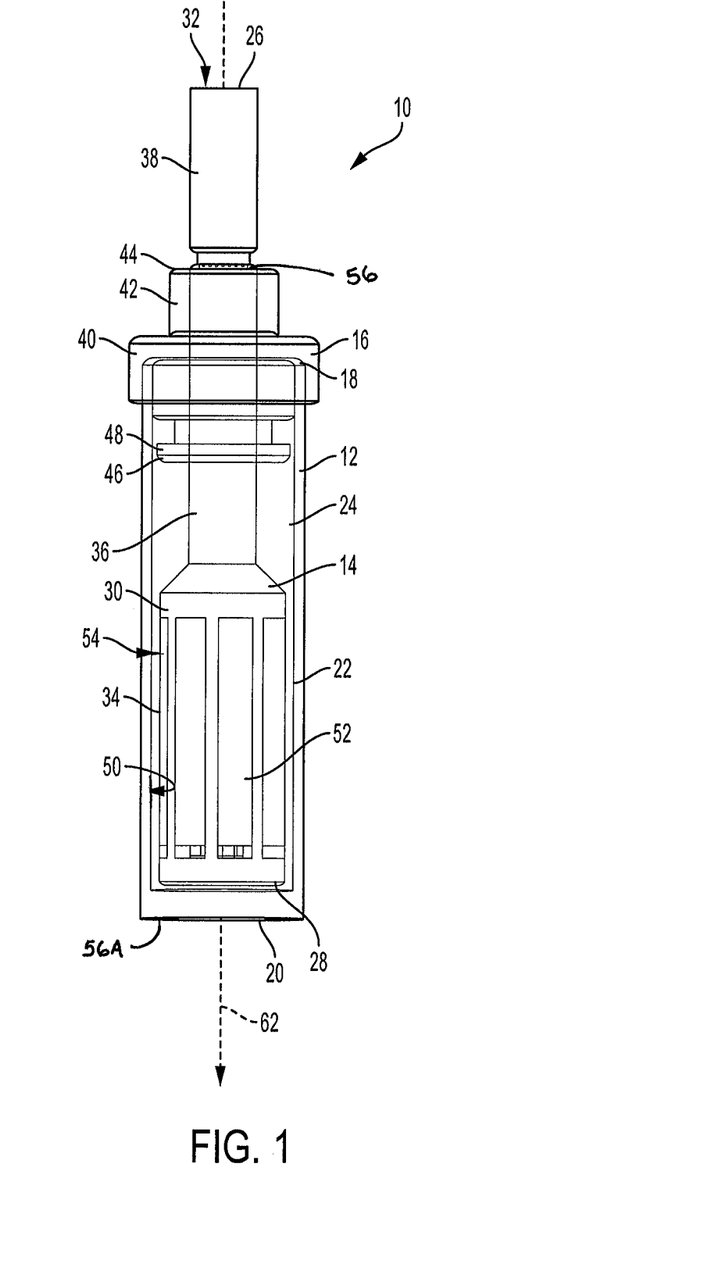
FIG. 1 is a partially transparent side view of a first embodiment of a filtration cell according to the present invention.
Figure 2:
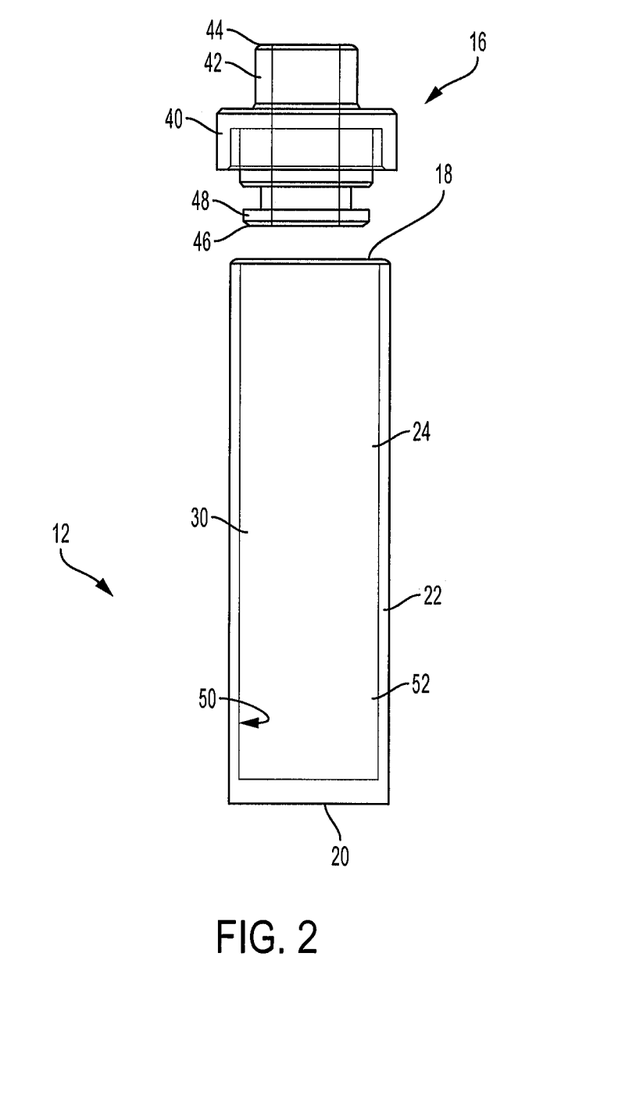
FIG. 2 is a partially transparent side view of the outer housing and the closure of the filtration cell of FIG. 1.

The outer housing 12 may have an open first end 18, a closed second end 20, and a sidewall 22 extending therebetween. The sidewall 22 defines a first chamber 24. The outer housing may take any suitable shape but is preferably substantially cylindrical.

Figure 3:
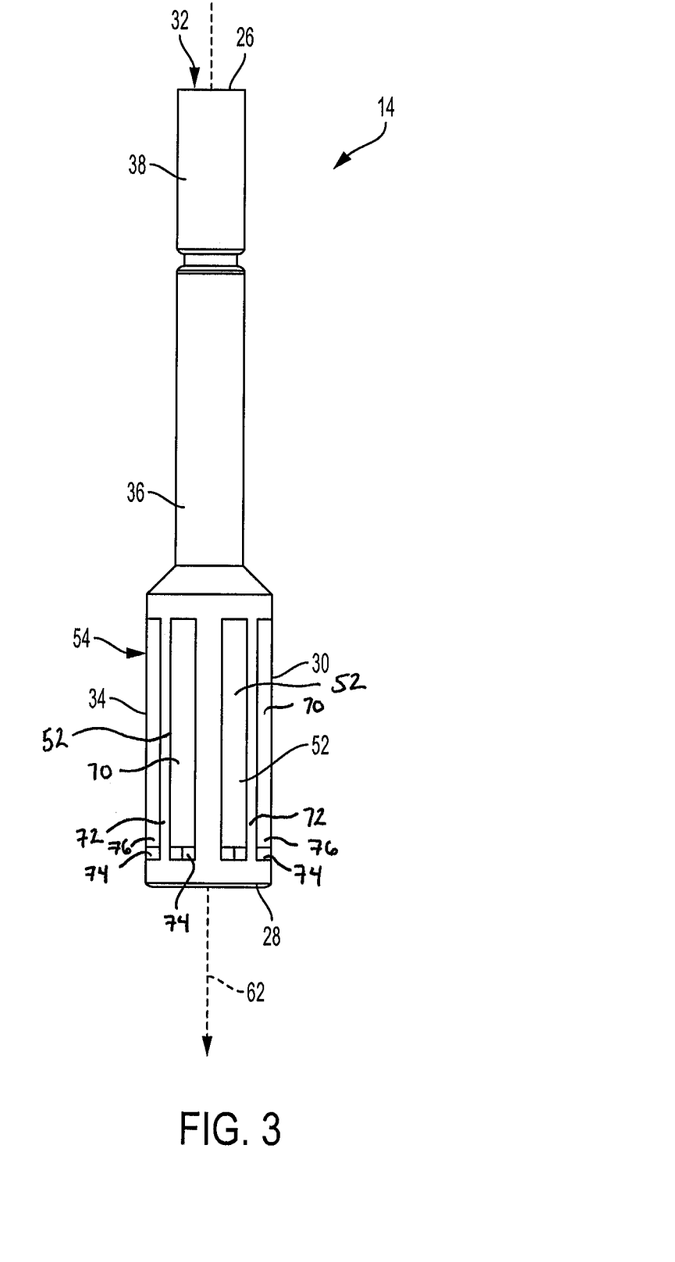
FIG. 3 is a side view of an inner housing of the filtration cell of FIG. 1.

The inner housing 14 may have a first end 26, a second end 28, and a sidewall 30 extending therebetween. The sidewall 30 defines a second chamber 32. The inner housing 14 may take any suitable shape but is preferably shaped to complimentarily be received within the interior of the outer housing 12. The inner housing 14 may have three portions, a filtering portion 34, a shaft portion 36, and an extension portion 38. The filtering portion 34 and at least a part of the shaft portion 36 of the inner housing 14 may be disposed within the first chamber 24 of the outer housing 12.

The closure 16 comprises a flange portion 40 and a central passageway 42 passing through the flange portion 40 and having a first end 44 and a second end 46. The flange portion 40 is adapted to be removably connected to the first open end 18 of the outer housing 12. The connection between the closure 16 and the outer housing 12 may take any suitable form including, but not limited to, a threaded connection and a snap-fit connection.

When the closure 16 is connected to the outer housing 12, the first end 44 of the central passageway 42 extends above the flange portion 40 of the closure 16 and outside of the first chamber 24 of the outer housing 12 and the second end 46 of the central passageway 42 extends below the flange portion 40 and inside of the first chamber 24 of the outer housing 12. The shaft portion 36 of the inner housing 14 extends through the central passageway 42 of the closure 16. At least the extension portion 38 of the inner housing 14 and, optionally, a part of the shaft portion 36 of the inner housing 14 extend beyond the first end 44 of the central passageway 42. In this manner, the closure 16 closes the first open end 18 of the outer housing 12 and the first end 26 of the inner housing 14 and holds them in a fixed position relative to one another, with the inner housing 14 at least partially received within the outer housing 12.

As shown in FIGS. 1 and 2, an annular seal 48 may be provided on the second end 46 of the central passageway 42 of the closure 16 to provide a seal between the inner surface 50 of the sidewall 22 of the outer housing 12 and the closure 16. Alternatively, the annular seal 48 may be provided adjacent the inner surface 50 of the sidewall 22 of the outer housing 12 to provide a seal between the inner surface 50 of the sidewall 22 of the outer housing 12 and the closure 16. The annular seal 48 may also provide a seal around the shaft portion 36 of the inner housing 14. The seal 48 may be air permeable and may be a hydrophobic porous material or simply a hydrophobic surface with a minimum gap which acts as a liquid barrier.

The filtering portion 34 of the inner housing 14 includes in the sidewall 30 at least one filtration membrane 52. In use, a biological specimen intended for separation into at least two components can be provided within the first chamber 24 in an initial sample receiving space defined between an inner surface 50 of the sidewall 22 of the outer housing 12 and an outer surface 54 of the inner housing 14. Upon application of rotation to at least a portion of the filtration cell 10, as will be discussed herein, a portion of the biological specimen held within the first chamber 24 can pass from the first chamber 24 into the second chamber 32, defined within the interior of the inner housing 14, through the filtration membrane 52. A plurality of filtration membranes 52 may be provided as shown in FIGS. 1, 3, 3A and 4A-5B.

The filtration membrane 52 may be made from any suitable material capable of filtering the biological sample including, but not limited to fibrous membranes and track etched membranes. For example, the filtration membrane 48 may be made from a track-etched membrane comprising a thin film including discrete pores. In certain embodiments, the film may be formed through a combination of charged particle bombardment or irradiation and chemical etching providing increased control over the pore size and density. More specifically, the filtration membrane 52 may be a polycarbonate track-etched membrane (PCTE membrane). In certain configurations, a track-etched membrane may have a thickness of about 10-12 μm. In other configurations, a fibrous membrane may have a thickness of >100 μm. In many sample separation procedures, a thinner membrane requires smaller initial sample collection volumes.

It is contemplated herein that the inner housing 14, specifically the filtering portion 34, may have many different configurations in which the filtration membrane 52 is supported by a housing element. The inner housing 14 may include different openings supporting a filtration membrane 52 across which a component of the biological specimen may pass while restraining at least another component of the biological sample. In one configuration, the filtration membrane 52 allows a plasma portion of a whole blood specimen to pass through the filtration membrane 52, while restraining the remaining portions of the whole blood specimen. As shown specifically in FIG. 3, the inner housing 14 includes a plurality of vertically disposed indentations 70 or non-cut through channels disposed within the sidewall 30 of the filtering portion 34. The filtration membrane 52 is supported across the indentations 70 by adjacent support regions 72. In one embodiment, an aperture 74 is provided at the bottom end 76 of at least one indentation 70. In one configuration, an aperture 74 is provided at the bottom end 76 of each indentation 70. As a first component of the biological sample, such as plasma, is separated across the filtration membrane 52, the separated component, such as plasma, flows along the indentations 70, which act like channels, and is directed into the apertures 74. The separated plasma passes through the apertures 74 and is collected within the second chamber 32 disposed within the interior of the inner housing 14. In one configuration, the filtration membrane 52 is disposed over both the indentations 70 and the apertures 74. In a further configuration, the filtration membrane 52 is wrapped around a substantial portion, such as the entirety of, the filtering portion 34, and is supported by the support regions 72.

Alternatively, the indentations 70 may be provided with a slit or vertical opening which extends along a portion of, or the entirety of, the indentation 70. The slit functions in the same manner as the aperture 74 in order to allow passage of the plasma into the second chamber 32 disposed within the interior of the inner housing 14 after it is separated by the filtration membrane 52.

Figure 3A:
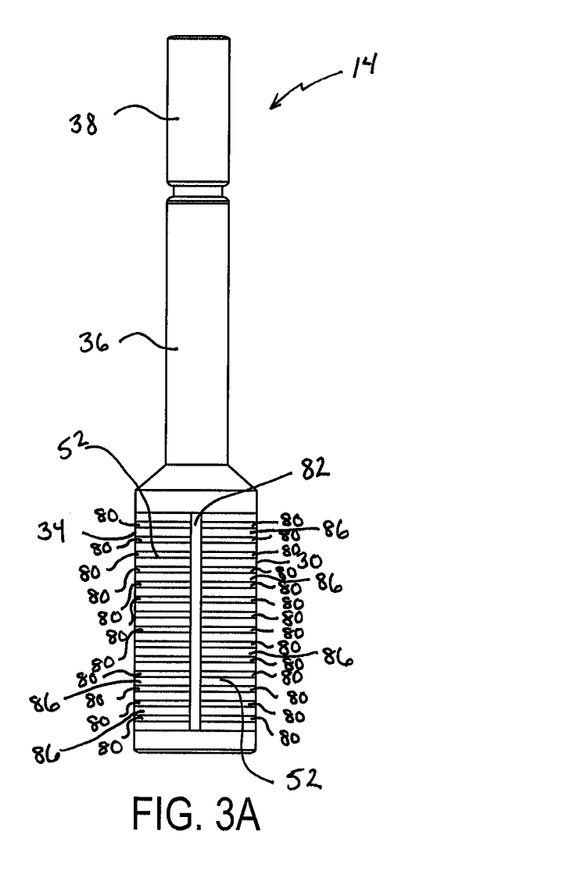
FIG. 3A is a side view of an alternative inner housing for receipt within the outer housing of FIG. 2.
Figure 3B:
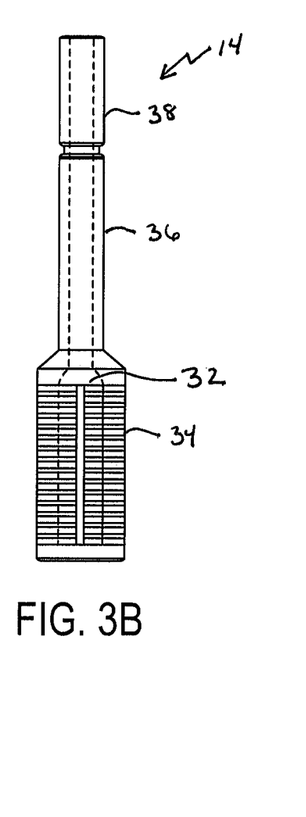
FIG. 3B is a side view of the inner housing of FIG. 3A illustrating the interior spacing.
Figure 3C:
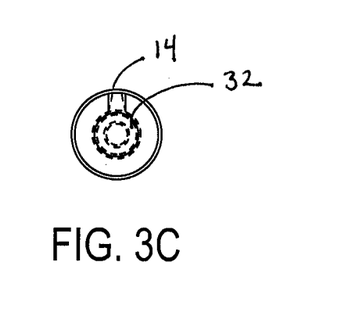
FIG. 3C is a top view of the inner housing of FIG. 3A.

In a further configuration, as shown in FIG. 3A-3C, the inner housing 14 includes a filtering portion 34 including a plurality of horizontally disposed indentations 80 or non-cut through channels disposed within the sidewall 30. A plurality of vertically disposed apertures 82 or cut-through channels are also disposed adjacent the horizontally disposed indentations 80. In one configuration, the inner housing 14 includes one vertically disposed aperture 82. In a further configuration, the inner housing 14 includes two vertically disposed apertures 82. In yet a further configuration, the inner housing 14 includes a plurality of vertically disposed apertures 82. The vertically disposed apertures 82 function similarly to the apertures 74, as described above, and allow plasma separated by the filtration membrane 52 to pass therethrough into the second chamber 32 within the interior of the inner housing 14. The horizontally disposed indentations 80 are intended to terminate into the vertically disposed aperture 82, such that plasma may freely flow through the horizontally disposed indentation 80 and into the vertically disposed aperture 82. In one configuration, the horizontally disposed indentations 80 are defined adjacent horizontally disposed support elements 86. These support elements 86 support the filtration membrane 52 along most of the circumference of the filtering portion 34, such as along almost the entirety of the perimeter of the filtering portion 34.

The outer housing 14 may include a port 56 in the sidewall 22 or a port 56A the closed second end 20 to allow a biological specimen intended for separation to be placed in first chamber 24 between an inner surface 50 of the sidewall 22 of the outer housing 12 and an outer surface 54 of the inner housing 14. The port 56 may be closed by a removable closure such including, but not limited to a plug. The outer housing 14 may also include grooves on the inner surface 50 of the sidewall 22 of the outer housing in order to promote mixing of the biological specimen, such as with a sample stabilizer.

In order to effect separation across the filtration membrane 52, at least one of the inner housing 14 and the outer housing 12 is rotatable with respect to the other of the inner housing 14 and the outer housing 12. Rotation of one of the inner housing 14 and the outer housing 12 with respect to the other of the inner housing 14 and the outer housing 12, creates a rotational fluid force which allows the specimen received within the first chamber 24 to contact the filtration membrane 52 and to allow a component or the specimen, such as plasma, be forced through the filtration membrane 52.

Figure 4A:
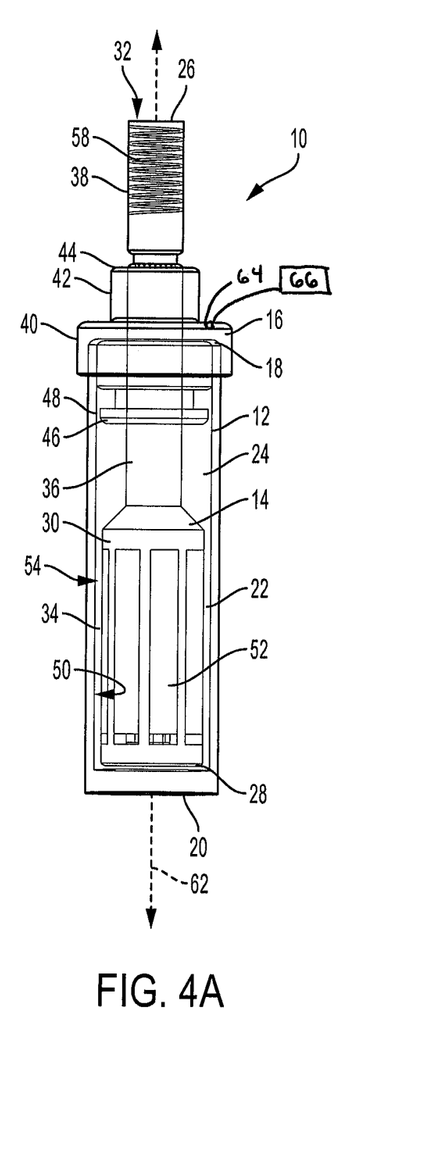
FIGS. 4A and 4B are partially transparent side views of a second embodiment of a filtration cell according to the present invention having a compressed spring driving mechanism in the pre-release and after release condition, respectively.
Figure 4B:
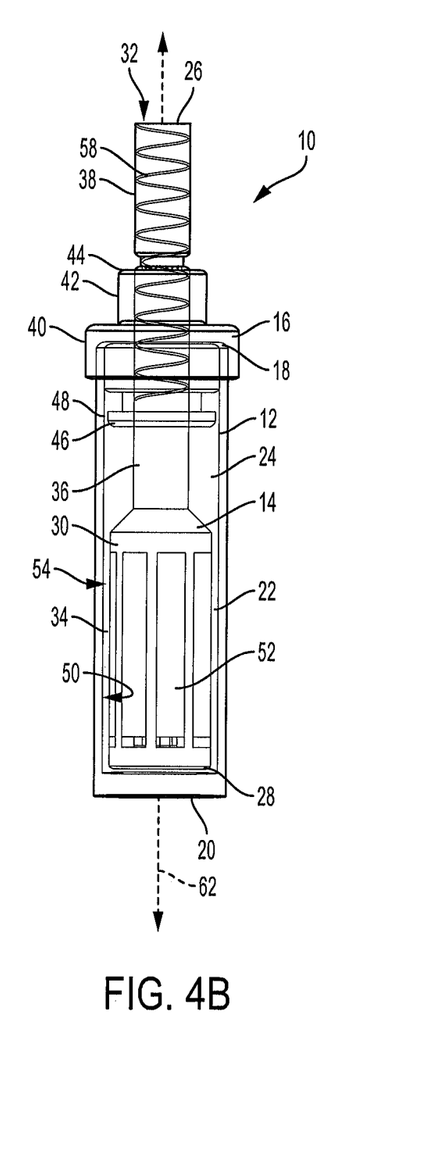
Figure 5A:
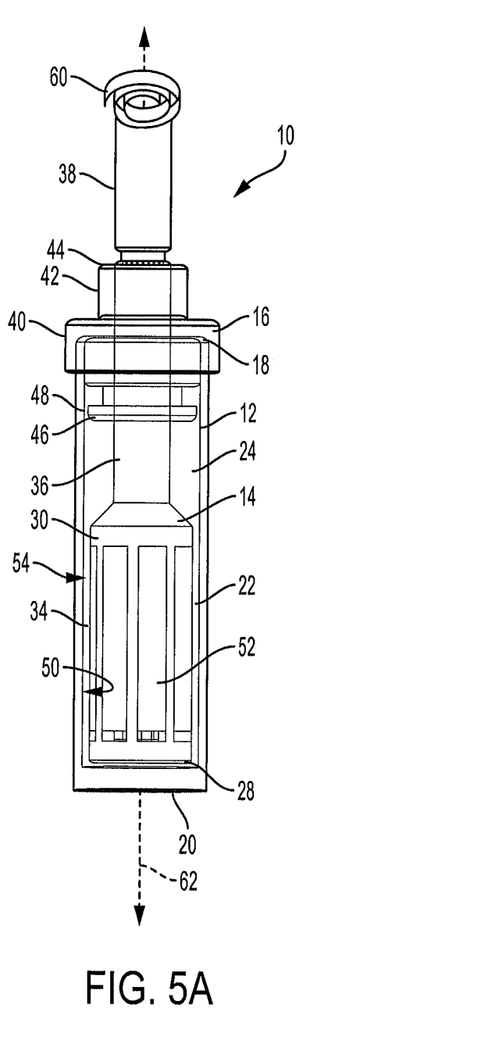
FIGS. 5A and 5B are partially transparent side views of a third embodiment of a filtration cell according to the present invention having a torsional spring driving mechanism in the pre-release and after release condition, respectively.
Figure 5B:
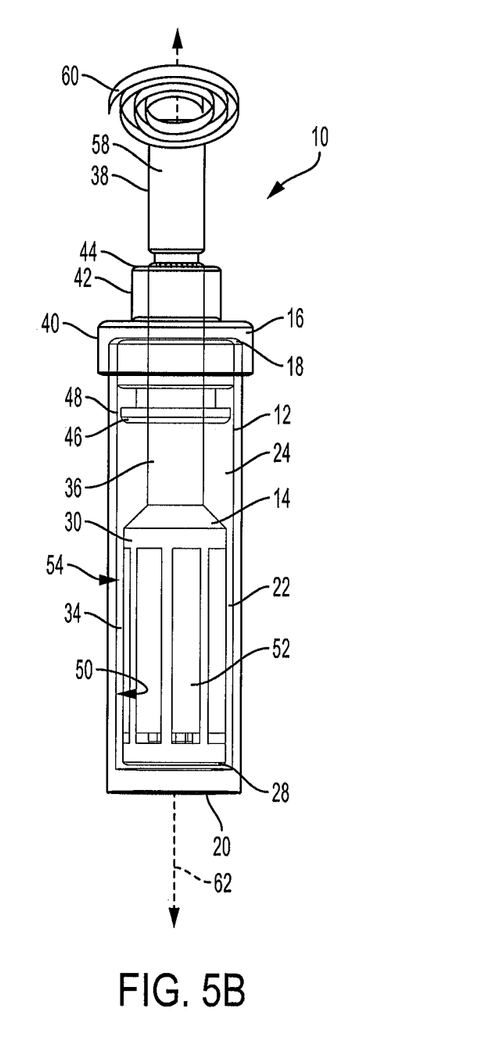

Rotation of the inner housing 14 with respect to the outer housing 12 may occur by rotating either the inner housing 14 or the outer housing 12. Rotation of the inner housing 14 or the outer housing 12 may be accomplished using any suitable means including, but not limited to, an air-powered motor, an electric motor, a pneumatic motor, and a mechanical motor. Optionally, such motors may be battery powered. A compressed spring 58, as shown in FIGS. 4A and 4B, or a torsional spring 60, as shown in FIGS. 5A and 5B, may be used. Alternatively, the inner housing 14 or the outer housing 12 may be rotated manually. If the inner housing 14 is being rotated, the rotation device may be attached to the extension portion 38 of the inner housing 14 while the outer housing 12 is held in a stationary position. Alternatively, if the outer housing 12 is being rotated, the rotation device may be attached to the outer housing 12 while the inner housing 14 is held in a stationary position. Rotation of the inner housing 14 with respect to the outer housing 12 may be coaxial as shown in FIGS. 1 and 4A-5B or may be non-coaxial.

Optionally, the inner housing 14 may be moved in an up and down motion in a direction parallel to its longitudinal axis 62.

An opening 64 to which a pressure unit 66 may be connected may be provided in the outer housing 12 or through the closure 16 into the first chamber 24 or the second chamber 32 in order to provide and regulate trans-membrane pressure by introducing a positive pressure in the first chamber 24 or by creating a vacuum in the second chamber 32.

In use, a sample, for example, whole blood, in placed in the first chamber 24 between an inner surface 50 of the sidewall 22 of the outer housing 12 and an outer surface 54 of the inner housing 14. Either the inner housing 14 is rotated with respect to the outer housing 12 or the outer housing 12 is rotated with respect to the inner housing 14 causing a tangential flow of the sample over the filtration membrane 52. During rotation and movement of the sample over the filtration membrane 52 of the inner housing 14, a portion of the sample, for example, the plasma portion of a whole blood sample, passes through the filtration membrane 52 into the second chamber 32.

In another embodiment, the filtration cell may have a distance from the first open end of the outer housing to the second closed end of the outer housing is smaller than a diameter of the outer housing and the distance from the first end of the inner housing to the second end of the inner housing is smaller than a diameter of the inner housing such that the outer housing and the inner housing have a disc shape. In this embodiment, the filtration membrane is included on the second end of the inner housing which includes a filtration portion and an extension portion. The extension portion extends from the first end of the inner housing.

In another embodiment, the filtration cell is very similar to the filtration cell 10 shown FIGS. 1-5B. The filtration cell includes an outer housing, an inner housing, a closure, and a rotation element. All elements identified herein with respect to this second embodiment are identical to those described above.

The outer housing may have an open first end, a closed second end, and a sidewall extending therebetween. The sidewall defines a first chamber. The outer housing may take any suitable shape but is preferably cylindrical.

The inner housing may have a first end, a second end, and a sidewall extending therebetween. The sidewall defines a second chamber. The inner housing may take any suitable shape but is preferably cylindrical. The inner housing is disposed within the first chamber of the outer housing.

The closure comprises a flange portion and a central passageway passing through the flange portion and having a first end and a second end. The flange portion is adapted to be removably connected to the first open end of the outer housing. The connection between the closure and the outer housing may take any suitable form including, but not limited to, a threaded connection and a snap-fit connection.

The rotation element may have a first end and a second end and may take any suitable shape including, but not limited to, cylindrical.

When the closure is connected to the first housing, the first end of the central passageway extends above the flange portion of the closure and outside of the first chamber of the outer housing and the second end of the central passageway extends below the flange portion and inside of the first chamber of the outer housing. The first end of the rotation element extends through the central passageway of the closure and the second end of the rotation element is located in the second chamber.

The inner housing includes at least one filtration membrane in the sidewall such that at least a portion of a biological sample placed in the second chamber can pass from the second chamber to the first chamber through the filtration membrane. A plurality of filtration membranes may be provided.

The outer housing may include a port in the sidewall or the closed second end to allow the filtrate to be removed from the first chamber. The port may be closed by a removable closure such including, but not limited to a plug.

The rotation element is rotatable with respect to the outer housing, the inner housing, and the closure. Rotation of the rotation element with respect to the inner housing may be accomplished using any suitable means including, but not limited to, an electric motor, a pneumatic motor, and a mechanical motor. Such motors may be battery powered. A compressed spring or a torsional spring may be used. Alternatively, the rotation element may be rotated manually.

Optionally, the rotation element may be moved in an up and down motion in a direction parallel to its longitudinal axis.

An opening to which a pressure unit may be connected may be provided in the outer housing or through the closure into the first chamber or the second chamber in order to provide and regulate trans-membrane pressure by introducing a positive pressure in the second chamber or by creating a vacuum in the first chamber.

In use, a sample, for example, whole blood, in placed in the second chamber. The rotation element is rotated with respect to the inner housing causing a tangential flow of the sample over the filtration membrane. During rotation and movement of the sample over the filtration membrane of the inner housing, a portion of the sample, for example, the plasma portion of a whole blood sample, passes through the filtration membrane into the first chamber.

In another embodiment, the filtration cell may have a distance from the first open end of the outer housing to the second closed end of the outer housing that is smaller than a diameter of the outer housing, a distance from the first end of the inner housing to the second end of the inner housing that is smaller than a diameter of the inner housing, and a distance from the first end of the rotation element to the second end of the rotation element that is smaller than a diameter of the rotation element such that the filtration cell has a disc shape. In this embodiment, the filtration membrane is included on the second end of the inner housing.

While specific embodiments of the device of the present disclosure have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the device of the present disclosure which is to be given the full breadth of the claims appended and any and all equivalents thereof.

The invention claimed is:

1. A filtration cell for a biological sample comprising:
   an outer housing having a first end, a second end, and a sidewall extending therebetween, the sidewall defining a first chamber; and
   an inner housing having a first end, a second end, at least one aperture, at least one indentation terminating into the at least one aperture and disposed within a sidewall of the inner housing, the sidewall of the inner housing defining a second chamber, the inner housing being disposed within the first chamber and rotatable with respect to the outer housing and the at least one aperture providing an opening into the second chamber,
   wherein at least a portion of the inner housing comprises a filtration membrane wherein the filtration membrane is disposed over the at least one aperture.

2. The filtration cell of claim 1, wherein upon rotation of the inner housing with respect to the outer housing, the filtration membrane is adapted to allow a first portion of the biological sample to pass from the first chamber into the second chamber and to restrain a second portion of the biological sample in the first chamber.

3. The filtration cell of claim 1 further comprising a closure sealing the first end of the outer housing and the first end of the inner housing.

4. The filtration cell of claim 1, wherein rotation of the inner housing with respect to the outer housing causes a tangential flow of the biological sample contained in the first chamber over the filtration membrane of the inner housing.

5. The filtration cell of claim 1, wherein a pressure differential is created across the filtration membrane by introducing a positive pressure into the first chamber or by introducing a vacuum in the second chamber.

6. The filtration cell of claim 1, further comprising at least one support region adjacent the indentation for supporting at least a portion of the filtration membrane.

7. The filtration cell of claim 1, wherein a rotation axis of the inner housing is coaxial with a central axis of the outer housing.

8. The filtration cell of claim 1, wherein a rotation axis of the inner housing is offset from a central axis of the outer housing.

9. The filtration cell of claim 1, wherein the inner housing is movable in a direction parallel to a central axis of the outer housing.

10. The filtration cell of claim 1, wherein the outer housing further comprises a port for receiving the biological sample.

11. The filtration cell of claim 1 further comprising a liquid seal between an interior surface of the sidewall of the outer housing and an exterior surface of the sidewall of the inner housing.

12. The filtration cell of claim 1 further comprising a biasing member that rotationally biases the inner housing with respect to the outer housing.

13. The filtration cell of claim 12, wherein the biasing member is a compression spring or a torsional spring.

14. The filtration cell of claim 1, wherein a distance from the first end of the outer housing to the second end of the outer housing is larger than a diameter of the outer housing and a distance from the first end of the inner housing to the second end of the inner housing is larger than a diameter of the inner housing.

15. The filtration cell of claim 1, wherein a distance from the first end of the outer housing to the second end of the outer housing is smaller than a diameter of the outer housing and a distance from the first end of the inner housing to the second end of the inner housing is smaller than a diameter of the inner housing.

16. The filtration cell of claim 1, wherein the filtration membrane is a track-etched membrane or a fibrous membrane.

17. The filtration cell of claim 1, further comprising:
   a rotation element engaged with at least one of the outer housing and the inner housing for rotating at least one of the outer housing and the inner housing with respect to the other of the outer housing and the inner housing.

18. The filtration cell of claim 17, wherein upon rotation of the rotation element, the filtration membrane is adapted to allow a first portion of the biological sample to pass from the first chamber into the second chamber and to restrain a second portion of the biological sample in the second chamber.

19. The filtration cell of claim 17, wherein a pressure differential is created across the filtration membrane by introducing a positive pressure into the second chamber or by introducing a vacuum in the second chamber.

20. The filtration cell of claim 17, wherein a rotation axis of the rotation element is coaxial with a central axis of the inner housing.

21. The filtration cell of claim 17, wherein the outer housing further comprises a port for extracting a filtered portion of the biological sample.

22. The filtration cell of claim 17, further comprising a biasing member that provides a rotational force to the rotation element.

* * * * *